(12) United States Patent
Kronman et al.

(10) Patent No.: US 10,292,570 B2
(45) Date of Patent: May 21, 2019

(54) SYSTEM AND METHOD FOR GUIDING AND TRACKING A REGION OF INTEREST USING AN ENDOSCOPE

(71) Applicant: EndoChoice, Inc., Alpharetta, GA (US)

(72) Inventors: Achia Kronman, Pardes Hana (IL); Ron Sharoni, Hadera (IL)

(73) Assignee: EndoChoice, Inc., Alpharetta, GA (US)

( * ) Notice: Subject to any disclaimer, the term of this patent is extended or adjusted under 35 U.S.C. 154(b) by 105 days.

(21) Appl. No.: 15/458,239

(22) Filed: Mar. 14, 2017

(65) Prior Publication Data

US 2017/0258295 A1 Sep. 14, 2017

Related U.S. Application Data

(60) Provisional application No. 62/307,779, filed on Mar. 14, 2016.

(51) Int. Cl.
*G02B 21/32* (2006.01)
*A61B 1/00* (2006.01)
(Continued)

(52) U.S. Cl.
CPC ........ *A61B 1/0005* (2013.01); *A61B 1/00009* (2013.01); *A61B 1/0016* (2013.01);
(Continued)

(58) Field of Classification Search
CPC .................................................... G02B 21/32
See application file for complete search history.

(56) References Cited

U.S. PATENT DOCUMENTS 3,639,714 A 2/1972 Fujimoto
3,955,064 A 5/1976 Demetrio
(Continued)

FOREIGN PATENT DOCUMENTS

CA 2297986 3/1999
CA 2765559 12/2010
(Continued)

OTHER PUBLICATIONS

Notice of Allowance dated Apr. 18, 2017 for U.S. Appl. No. 13/713,449.
(Continued)

*Primary Examiner* — Pankaj Kumar
*Assistant Examiner* — Timothy R Newlin
(74) *Attorney, Agent, or Firm* — Bookoff McAndrews, PLLC

(57) ABSTRACT

A system and method of repositioning a region of interest within an endoscopic image from a first location to a target location on the display screen of an endoscopy system is provided. The endoscopy system includes an insertion portion having a tip section with at least one viewing element for capturing images of a body cavity having the region of interest. The method includes detecting a region of interest within a body cavity, displaying the region of interest on a display screen in communication with the endoscopy system, marking the region of interest on the display screen, selecting a target location on the display screen, estimating a transformation to be applied to the region of interest, and applying the estimated transformation for causing the region of interest to be displayed at the target location of the display screen.

19 Claims, 8 Drawing Sheets

(51) Int. Cl.
*A61B 1/018* (2006.01)
*A61B 1/05* (2006.01)
*A61B 1/06* (2006.01)
*G06F 3/0484* (2013.01)
*H04N 5/225* (2006.01)
*A61B 34/20* (2016.01)

(52) U.S. Cl.
CPC ...... *A61B 1/00039* (2013.01); *A61B 1/00114* (2013.01); *A61B 1/018* (2013.01); *A61B 1/05* (2013.01); *A61B 1/06* (2013.01); *G06F 3/04842* (2013.01); *H04N 5/2256* (2013.01); *A61B 2034/2055* (2016.02); *H04N 2005/2255* (2013.01)

(56) References Cited

U.S. PATENT DOCUMENTS

| | | |
|---|---|---|
| 4,027,697 A | 6/1977 | Bonney |
| 4,037,588 A | 7/1977 | Heckele |
| 4,084,401 A | 4/1978 | Belardi |
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,874,220 A * | 10/1989 | Yamagata ......... G02B 23/2407 385/33 |
| 4,877,314 A | 10/1989 | Kanamori |
| 4,891,696 A * | 1/1990 | Miyazaki ........... H04N 5/23248 348/571 |
| 4,902,115 A | 2/1990 | Takahashi |
| 4,935,810 A * | 6/1990 | Nonami ............. A61B 1/00193 348/45 |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,475,420 A | 12/1995 | Buchin |
| 5,489,256 A | 2/1996 | Adair |
| 5,518,501 A | 5/1996 | Oneda |
| 5,518,502 A | 5/1996 | Kaplan |
| 5,547,455 A | 8/1996 | McKenna |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,630,798 A | 5/1997 | Beiser |
| 5,662,588 A | 9/1997 | Iida |
| 5,669,871 A * | 9/1997 | Sakiyama ................. A61B 1/05 348/135 |
| 5,674,182 A | 10/1997 | Suzuki |
| 5,685,821 A | 11/1997 | Pike |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,800,341 A | 9/1998 | McKenna |
| 5,810,715 A | 9/1998 | Moriyama |
| 5,810,717 A | 9/1998 | Maeda |
| 5,810,770 A | 9/1998 | Chin |
| 5,830,121 A | 11/1998 | Enomoto |
| 5,836,894 A | 11/1998 | Sarvazyan |
| 5,860,913 A | 1/1999 | Yamaya |
| 5,870,234 A | 2/1999 | EbbesmeierneeSchitthof |
| 5,916,148 A | 6/1999 | Tsuyuki |
| 5,940,126 A | 8/1999 | Kimura |
| 6,058,109 A | 5/2000 | Lechleider |
| 6,095,970 A | 8/2000 | Hidaka |
| 6,095,971 A | 8/2000 | Takahashi |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,409,658 B1 * | 6/2002 | Mitsumori ......... A61B 1/00096 600/130 |
| 6,419,626 B1 | 7/2002 | Yoon |
| 6,476,851 B1 | 11/2002 | Nakamura |
| 6,520,908 B1 | 2/2003 | Ikeda |
| 6,636,254 B1 | 10/2003 | Onishi |
| 6,638,214 B2 | 10/2003 | Akiba |
| 6,673,012 B2 | 1/2004 | Fujii |
| 6,690,337 B1 | 2/2004 | Mayer, III |
| 6,712,760 B2 | 3/2004 | Sano |
| 6,832,984 B2 | 12/2004 | Stelzer |
| 6,888,119 B2 | 5/2005 | Iizuka |
| 6,977,678 B1 * | 12/2005 | Wada ................. G08B 13/1963 348/143 |
| 6,997,871 B2 | 2/2006 | Sonnenschein |
| 7,154,378 B1 | 12/2006 | Ertas |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,918,788 B2 | 4/2011 | Lin |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,248,413 B2 | 8/2012 | Gattani |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,353,860 B2 | 1/2013 | Boulais |
| 8,447,132 B1 | 5/2013 | Galil |
| 8,449,457 B2 | 5/2013 | Aizenfeld |
| 8,460,182 B2 | 6/2013 | Ouyang |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,144,664 B2 | 9/2015 | Jacobsen |
| 9,289,110 B2 | 3/2016 | Woolford |
| 9,314,147 B2 | 4/2016 | Levy |
| 9,320,419 B2 | 4/2016 | Kirma |

(56) References Cited

U.S. PATENT DOCUMENTS

| | | |
|---|---|---|
| 9,329,375 B2 * | 5/2016 | Zuest ............. G02B 21/0016 |
| 2001/0036322 A1 | 11/2001 | Bloomfield |
| 2002/0010384 A1 * | 1/2002 | Shahidi ............. A61B 1/00009 |
| | | 600/118 |
| 2002/0017515 A1 | 2/2002 | Obata |
| 2002/0047897 A1 | 4/2002 | Sugimoto |
| 2002/0087047 A1 | 7/2002 | Remijan |
| 2002/0109771 A1 | 8/2002 | Ledbetter |
| 2002/0109774 A1 | 8/2002 | Meron |
| 2002/0161279 A1 | 10/2002 | Luloh |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0139650 A1 | 7/2003 | Homma |
| 2003/0153897 A1 | 8/2003 | Russo |
| 2003/0158503 A1 | 8/2003 | Matsumoto |
| 2003/0163029 A1 | 8/2003 | Sonnenschein |
| 2004/0015054 A1 | 1/2004 | Hino |
| 2004/0046865 A1 | 3/2004 | Ueno |
| 2004/0061780 A1 | 4/2004 | Huffman |
| 2004/0064019 A1 | 4/2004 | Chang |
| 2004/0077927 A1 | 4/2004 | Ouchi |
| 2004/0106850 A1 | 6/2004 | Yamaya |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2004/0260151 A1 | 12/2004 | Akiba |
| 2005/0018042 A1 | 1/2005 | Rovegno |
| 2005/0020876 A1 | 1/2005 | Shioda |
| 2005/0038317 A1 | 2/2005 | Ratnakar |
| 2005/0041282 A1 * | 2/2005 | Rudolph ............. G02B 7/001 |
| | | 359/368 |
| 2005/0047134 A1 | 3/2005 | Mueller |
| 2005/0057687 A1 | 3/2005 | Irani |
| 2005/0090709 A1 | 4/2005 | Okada |
| 2005/0096501 A1 | 5/2005 | Stelzer |
| 2005/0119527 A1 | 6/2005 | Banik |
| 2005/0124858 A1 | 6/2005 | Matsuzawa |
| 2005/0222499 A1 | 10/2005 | Banik |
| 2005/0234296 A1 | 10/2005 | Saadat |
| 2005/0234347 A1 | 10/2005 | Yamataka |
| 2005/0251127 A1 | 11/2005 | Brosch |
| 2005/0272975 A1 | 12/2005 | McWeeney |
| 2005/0277808 A1 | 12/2005 | Sonnenschein |
| 2005/0283048 A1 | 12/2005 | Gill |
| 2006/0004257 A1 | 1/2006 | Gilad |
| 2006/0047184 A1 | 3/2006 | Banik |
| 2006/0063976 A1 | 3/2006 | Aizenfeld |
| 2006/0069314 A1 | 3/2006 | Farr |
| 2006/0111613 A1 | 5/2006 | Boutillette |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0197839 A1 * | 9/2006 | Senior ............. H04N 5/232 |
| | | 348/169 |
| 2006/0215406 A1 | 9/2006 | Thrailkill |
| 2006/0235306 A1 | 10/2006 | Cotter |
| 2006/0252994 A1 | 11/2006 | Ratnakar |
| 2006/0264704 A1 | 11/2006 | Fujimori |
| 2006/0293556 A1 | 12/2006 | Gamer |
| 2007/0015989 A1 | 1/2007 | Desai |
| 2007/0049803 A1 | 3/2007 | Moriyama |
| 2007/0055100 A1 | 3/2007 | Kato |
| 2007/0055128 A1 | 3/2007 | Glossop |
| 2007/0079029 A1 | 4/2007 | Carlson |
| 2007/0088193 A1 | 4/2007 | Omori |
| 2007/0100206 A1 | 5/2007 | Lin |
| 2007/0106119 A1 | 5/2007 | Hirata |
| 2007/0118015 A1 | 5/2007 | Wendlandt |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0241895 A1 | 10/2007 | Morgan |
| 2007/0244353 A1 | 10/2007 | Larsen |
| 2007/0244354 A1 | 10/2007 | Bayer |
| 2007/0247867 A1 | 10/2007 | Hunter |
| 2007/0249907 A1 | 10/2007 | Boulais |
| 2007/0265492 A1 | 11/2007 | Sonnenschein |
| 2007/0265498 A1 | 11/2007 | Ito |
| 2007/0270642 A1 | 11/2007 | Bayer |
| 2007/0270650 A1 * | 11/2007 | Eno ............. A61B 1/00045 |
| | | 600/145 |
| 2007/0279486 A1 | 12/2007 | Bayer |
| 2007/0286764 A1 | 12/2007 | Noguchi |
| 2007/0293720 A1 | 12/2007 | Bayer |
| 2008/0009673 A1 | 1/2008 | Khachi |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 * | 2/2008 | Yasushi ............. A61B 1/00096 |
| | | 600/175 |
| 2008/0058601 A1 | 3/2008 | Fujimori |
| 2008/0071143 A1 * | 3/2008 | Gattani ............. A61B 1/00009 |
| | | 600/117 |
| 2008/0071290 A1 | 3/2008 | Larkin |
| 2008/0091065 A1 | 4/2008 | Oshima |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0246771 A1 | 10/2008 | Oneal |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0076327 A1 | 3/2009 | Ohki |
| 2009/0082624 A1 | 3/2009 | Joko |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0209811 A1 | 8/2009 | Higuchi |
| 2009/0213211 A1 | 8/2009 | Bayer |
| 2009/0216084 A1 | 8/2009 | Yamane |
| 2009/0225159 A1 | 9/2009 | Schneider |
| 2009/0231419 A1 | 9/2009 | Bayer |
| 2009/0234183 A1 | 9/2009 | Abe |
| 2009/0248036 A1 * | 10/2009 | Hoffman ............. A61B 1/045 |
| | | 606/130 |
| 2009/0250501 A1 * | 10/2009 | Sonnenschein .... A61B 17/0057 |
| | | 227/176.1 |

(56) References Cited

U.S. PATENT DOCUMENTS

| | | | |
|---|---|---|---|
| 2009/0253966 A1 | 10/2009 | Ichimura | |
| 2009/0287188 A1 | 11/2009 | Golden | |
| 2009/0287192 A1 | 11/2009 | Vivenzio | |
| 2009/0299144 A1 | 12/2009 | Shigemori | |
| 2010/0010309 A1 | 1/2010 | Kitagawa | |
| 2010/0016673 A1 | 1/2010 | Bandy | |
| 2010/0053312 A1 | 3/2010 | Watanabe | |
| 2010/0069713 A1 | 3/2010 | Endo | |
| 2010/0073470 A1 | 3/2010 | Takasaki | |
| 2010/0073948 A1 | 3/2010 | Stein | |
| 2010/0076268 A1 | 3/2010 | Takasugi | |
| 2010/0123950 A1 | 5/2010 | Fujiwara | |
| 2010/0130822 A1 | 5/2010 | Katayama | |
| 2010/0141763 A1 | 6/2010 | Itoh | |
| 2010/0160729 A1 | 6/2010 | Smith | |
| 2010/0174144 A1 | 7/2010 | Hsu | |
| 2010/0231702 A1 | 9/2010 | Tsujimura | |
| 2010/0245653 A1 | 9/2010 | Bodor | |
| 2010/0249513 A1 | 9/2010 | Tydlaska | |
| 2010/0280322 A1 | 11/2010 | Mizuyoshi | |
| 2010/0296178 A1 | 11/2010 | Genet | |
| 2010/0326703 A1 | 12/2010 | Gilad | |
| 2011/0004058 A1 | 1/2011 | Oneda | |
| 2011/0004059 A1 | 1/2011 | Arneson | |
| 2011/0034769 A1 | 2/2011 | Adair | |
| 2011/0063427 A1 | 3/2011 | Fengler | |
| 2011/0084835 A1 | 4/2011 | Whitehouse | |
| 2011/0134517 A1* | 6/2011 | Shirota | G02B 21/24 359/381 |
| 2011/0140003 A1 | 6/2011 | Beck | |
| 2011/0160530 A1 | 6/2011 | Ratnakar | |
| 2011/0160535 A1 | 6/2011 | Bayer | |
| 2011/0169931 A1 | 7/2011 | Pascal | |
| 2011/0184243 A1 | 7/2011 | Wright | |
| 2011/0211267 A1 | 9/2011 | Takato | |
| 2011/0254937 A1 | 10/2011 | Yoshino | |
| 2011/0263938 A1* | 10/2011 | Levy | A61B 1/00091 600/109 |
| 2011/0282144 A1 | 11/2011 | Gettman | |
| 2011/0292258 A1 | 12/2011 | Adler | |
| 2012/0040305 A1 | 2/2012 | Karazivan | |
| 2012/0050606 A1 | 3/2012 | Debevec | |
| 2012/0053407 A1 | 3/2012 | Levy | |
| 2012/0057251 A1 | 3/2012 | Takato | |
| 2012/0065468 A1 | 3/2012 | Levy | |
| 2012/0075444 A1* | 3/2012 | Rovegno | H04N 7/183 348/65 |
| 2012/0076425 A1 | 3/2012 | Brandt | |
| 2012/0119879 A1* | 5/2012 | Estes | G08B 13/19641 340/8.1 |
| 2012/0162402 A1 | 6/2012 | Amano | |
| 2012/0200683 A1 | 8/2012 | Oshima | |
| 2012/0209071 A1 | 8/2012 | Bayer | |
| 2012/0209289 A1 | 8/2012 | Duque | |
| 2012/0212630 A1 | 8/2012 | Pryor | |
| 2012/0220832 A1 | 8/2012 | Nakade | |
| 2012/0224026 A1 | 9/2012 | Bayer | |
| 2012/0229615 A1 | 9/2012 | Kirma | |
| 2012/0232340 A1 | 9/2012 | Levy | |
| 2012/0232343 A1 | 9/2012 | Levy | |
| 2012/0253121 A1 | 10/2012 | Kitano | |
| 2012/0277535 A1 | 11/2012 | Hoshino | |
| 2012/0281536 A1 | 11/2012 | Gell | |
| 2012/0289858 A1 | 11/2012 | Ouyang | |
| 2012/0300999 A1 | 11/2012 | Bayer | |
| 2013/0053646 A1 | 2/2013 | Yamamoto | |
| 2013/0057724 A1 | 3/2013 | Miyahara | |
| 2013/0060086 A1 | 3/2013 | Talbert | |
| 2013/0066297 A1 | 3/2013 | Shtul | |
| 2013/0077257 A1 | 3/2013 | Tsai | |
| 2013/0085329 A1 | 4/2013 | Morrissette | |
| 2013/0109916 A1* | 5/2013 | Levy | A61B 1/042 600/109 |
| 2013/0116506 A1 | 5/2013 | Bayer | |
| 2013/0131447 A1 | 5/2013 | Benning | |
| 2013/0137930 A1 | 5/2013 | Menabde | |
| 2013/0141557 A1 | 6/2013 | Kawata | |
| 2013/0150671 A1 | 6/2013 | Levy | |
| 2013/0155178 A1* | 6/2013 | Mock | H04N 7/15 348/14.08 |
| 2013/0158344 A1 | 6/2013 | Taniguchi | |
| 2013/0169843 A1 | 7/2013 | Ono | |
| 2013/0172670 A1 | 7/2013 | Levy | |
| 2013/0172676 A1 | 7/2013 | Levy | |
| 2013/0197309 A1 | 8/2013 | Sakata | |
| 2013/0197556 A1 | 8/2013 | Shelton | |
| 2013/0222640 A1 | 8/2013 | Baek | |
| 2013/0253268 A1 | 9/2013 | Okada | |
| 2013/0264465 A1 | 10/2013 | Dai | |
| 2013/0267778 A1 | 10/2013 | Rehe | |
| 2013/0271588 A1 | 10/2013 | Kirma | |
| 2013/0274551 A1 | 10/2013 | Kirma | |
| 2013/0281925 A1 | 10/2013 | Benscoter | |
| 2013/0296649 A1 | 11/2013 | Kirma | |
| 2013/0303979 A1 | 11/2013 | Stieglitz | |
| 2013/0317295 A1 | 11/2013 | Morse | |
| 2014/0018624 A1 | 1/2014 | Bayer | |
| 2014/0031627 A1 | 1/2014 | Jacobs | |
| 2014/0046136 A1 | 2/2014 | Bayer | |
| 2014/0078241 A1* | 3/2014 | Vaisburd | H04N 7/147 348/14.08 |
| 2014/0107418 A1 | 4/2014 | Ratnakar | |
| 2014/0148644 A1 | 5/2014 | Levi | |
| 2014/0184766 A1 | 7/2014 | Amling | |
| 2014/0213850 A1 | 7/2014 | Levy | |
| 2014/0225998 A1 | 8/2014 | Dai | |
| 2014/0276207 A1 | 9/2014 | Ouyang | |
| 2014/0296628 A1 | 10/2014 | Kirma | |
| 2014/0296643 A1 | 10/2014 | Levy | |
| 2014/0296866 A1* | 10/2014 | Salman | A61B 1/018 606/109 |
| 2014/0298932 A1 | 10/2014 | Okamoto | |
| 2014/0309495 A1 | 10/2014 | Kirma | |
| 2014/0316198 A1 | 10/2014 | Krivopisk | |
| 2014/0316204 A1 | 10/2014 | Ofir | |
| 2014/0320617 A1 | 10/2014 | Parks | |
| 2014/0333742 A1 | 11/2014 | Salman | |
| 2014/0333743 A1 | 11/2014 | Gilreath | |
| 2014/0336459 A1 | 11/2014 | Bayer | |
| 2014/0343358 A1 | 11/2014 | Hameed | |
| 2014/0343361 A1 | 11/2014 | Salman | |
| 2014/0343489 A1 | 11/2014 | Lang | |
| 2014/0364691 A1 | 12/2014 | Krivopisk | |
| 2014/0364692 A1 | 12/2014 | Salman | |
| 2014/0364694 A1 | 12/2014 | Avron | |
| 2015/0005581 A1 | 1/2015 | Salman | |
| 2015/0045614 A1 | 2/2015 | Krivopisk | |
| 2015/0057500 A1 | 2/2015 | Salman | |
| 2015/0094536 A1 | 4/2015 | Wieth | |
| 2015/0099925 A1 | 4/2015 | Davidson | |
| 2015/0099926 A1 | 4/2015 | Davidson | |
| 2015/0105618 A1 | 4/2015 | Levy | |
| 2015/0164308 A1 | 6/2015 | Ratnakar | |
| 2015/0182105 A1 | 7/2015 | Salman | |
| 2015/0196190 A1 | 7/2015 | Levy | |
| 2015/0201827 A1 | 7/2015 | Sidar | |
| 2015/0208900 A1 | 7/2015 | Vidas | |
| 2015/0208909 A1 | 7/2015 | Davidson | |
| 2015/0223676 A1 | 8/2015 | Bayer | |
| 2015/0230698 A1 | 8/2015 | Cline | |
| 2015/0305601 A1 | 10/2015 | Levi | |
| 2015/0313445 A1 | 11/2015 | Davidson | |
| 2015/0313450 A1 | 11/2015 | Wieth | |
| 2015/0313451 A1 | 11/2015 | Salman | |
| 2015/0320300 A1 | 11/2015 | Gershov | |
| 2015/0342442 A1 | 12/2015 | Tadano | |
| 2015/0342446 A1 | 12/2015 | Levy | |
| 2015/0359415 A1 | 12/2015 | Lang | |
| 2015/0374206 A1 | 12/2015 | Shimony | |
| 2016/0006943 A1* | 1/2016 | Ratnakar | A61B 1/00009 348/36 |
| 2016/0015257 A1 | 1/2016 | Levy | |

(56) References Cited

U.S. PATENT DOCUMENTS

| | | | |
|---|---|---|---|
| 2016/0015258 A1 | 1/2016 | Levin | |
| 2016/0058268 A1 | 3/2016 | Salman | |
| 2017/0257619 A1* | 9/2017 | Kashima | A61B 1/04 |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 A1 | 12/2010 |
| WO | 2012038958 | 3/2012 |
| WO | 2012056453 A2 | 5/2012 |
| WO | 2012075153 A2 | 6/2012 |
| WO | 2012077116 | 6/2012 |
| WO | 2012077117 A1 | 6/2012 |
| WO | 2012096102 | 7/2012 |
| WO | 2012120507 A1 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015149041 A1 | 10/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

Office Action dated Apr. 19, 2017 for U.S. Appl. No. 14/988,551.
Notice of Allowability dated Apr. 21, 2017 for U.S. Appl. No. 14/549,265.
Office Action dated May 11, 2017 for U.S. Appl. No. 14/278,293.
Office Action dated May 10, 2017 for U.S. Appl. No. 14/998,551.
Office Action dated May 5, 2017 for U.S. Appl. No. 15/077,513.
Notice of Allowance dated May 15, 2017 for U.S. Appl. No. 14/271,270.
Office Action dated May 15, 2017 for U.S. Appl. No. 14/278,293.
Office Action dated May 18, 2017 for U.S. Appl. No. 14/278,338.
Notice of Allowance dated May 16, 2017 for U.S. Appl. No. 14/746,986.
Office Action dated May 23, 2017 for U.S. Appl. No. 13/655,120.
Notice of Allowance dated May 25, 2017 for U.S. Appl. No. 14/318,189.
Office Action dated May 23, 2017 for U.S. Appl. No. 14/500,975.
International Search Report for PCT/US14/37004, dated Sep. 25, 2014.
International Search Report for PCT/US14/38094, dated Nov. 6, 2014.

(56) References Cited

OTHER PUBLICATIONS

International Search Report for PCT/US2014/037526, dated Oct. 16, 2014.
International Search Report for PCT/US2014/071085, dated Mar. 27, 2015.
International Search Report for PCT/US2014/58143, dated Jan. 21, 2015.
International Search Report for PCT/US2015/012506, dated Dec. 11, 2015.
International Search Report for PCT/US2015/012751, dated Jun. 26, 2015.
International Search Report for PCT/US2015/027902, dated Jul. 23, 2015.
International Search Report for PCT/US2015/28962, dated Jul. 28, 2015.
International Search Report for PCT/US2015/29421, dated Aug. 7, 2015.
International Search Report for PCT/US2015/41396, dated Sep. 29, 2015.
International Search Report for PCT/US2015/47334, dated Dec. 28, 2015.
International Search Report for PCT/US2015/6548, dated Feb. 26, 2016.
International Search Report for PCT/US2015/66486, dated Dec. 17, 2015.
International Search Report for PCT/US2017/022236, dated May 25, 2017.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Feb. 26, 2016 for U.S. Appl. No. 14/274,323.
Office Action dated Feb. 4, 2016 for U.S. Appl. No. 14/271,234.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.
Office Action dated Jun. 30, 2016 for U.S. Appl. No. 13/655,120.
Office Action dated Jun. 28, 2016 for U.S. Appl. No. 14/278,293.
Office Action dated Jul. 1, 2016 for U.S. Appl. No. 14/229,699.
Office Action dated Jul. 15, 2016 for U.S. Appl. No. 14/273,923.
Notice of Allowance dated Jul. 15, 2016 for U.S. Appl. No. 14/274,323.
Office Action dated Jul. 22, 2016 for U.S. Appl. No. 14/549,265.
Sherman L.M., Plastic That Conduct Hear, Plastics Technology, Jun. 2001—article obtained online from http://www.ptonline.com/articles/plastics-that-conduct-heat.
Office Action dated Aug. 11, 2016 for U.S. Appl. No. 14/318,249.
Office Action dated Apr. 28, 2016 for U.S. Appl. No. 13/992,014.
Notice of Allowance dated Aug. 26, 2016 for U.S. Appl. No. 13/212,627.
Office Action dated Sep. 2, 2016 for U.S. Appl. No. 14/278,338.
Office Action dated Sep. 16, 2016 for U.S. Appl. No. 13/992,014.
Notice of Allowance dated Oct. 12, 2016 for U.S. Appl. No. 13/119,032.
Office Action dated Oct. 7, 2016 for U.S. Appl. No. 13/713,449.
Office Action dated Oct. 5, 2016 for U.S. Appl. No. 14/271,270.
Notice of Allowance dated Oct. 13, 2016 for U.S. Appl. No. 14/273,923.
Notice of Allowance dated Nov. 9, 2016 for U.S. Appl. No. 13/557,114.
Office Action dated Dec. 1, 2016 for U.S. Appl. No. 14/278,293.
Office Action dated Dec. 9, 2016 for U.S. Appl. No. 14/549,265.
Office Action dated Dec. 16, 2016 for U.S. Appl. No. 14/263,896.
Notice of Allowance dated Dec. 28, 2016 for U.S. Appl. No. 14/229,699.
Notice of Allowance dated Dec. 27, 2016 for U.S. Appl. No. 14/317,863.
Office Action dated Dec. 27, 2016 for U.S. Appl. No. 14/603,137.
Office Action dated Dec. 29, 2016 for U.S. Appl. No. 15/077,513.
Office Action dated Dec. 30, 2016 for U.S. Appl. No. 14/457,268.
Office Action dated Jan. 17, 2017 for U.S. Appl. No. 14/318,189.
Notice of Allowance dated Jan. 31, 2017 for U.S. Appl. No. 14/271,234.
Office Action dated Feb. 2, 2017 for U.S. Appl. No. 14/278,338.
Office Action dated Feb. 9, 2017 for U.S. Appl. No. 14/746,986.
Office Action dated Feb. 6, 2017 for U.S. Appl. No. 14/751,835.
Office Action dated Feb. 14, 2017 for U.S. Appl. No. 14/271,270.
Office Action dated Feb. 23, 2017 for U.S. Appl. No. 14/318,249.
Office Action dated Mar. 9, 2017 for U.S. Appl. No. 14/791,316.
Office Action dated Mar. 21, 2017 for U.S. Appl. No. 13/992,014.
Office Action dated Mar. 20, 2017 for U.S. Appl. No. 14/278,293.
Notice of Allowance dated Mar. 21, 2017 for U.S. Appl. No. 14/549,265.
Office Action dated Mar. 22, 2017 for U.S. Appl. No. 14/705,355.
Office Action dated Mar. 14, 2017 for U.S. Appl. No. 14/838,509.
Notice of Allowance dated Apr. 12, 2017 for U.S. Appl. No. 14/603,137.

* cited by examiner

"Move the Endoscope Proximally"

"Move the Endoscope Distally"

SYSTEM AND METHOD FOR GUIDING AND TRACKING A REGION OF INTEREST USING AN ENDOSCOPE

CROSS REFERENCE

The present application relies on U.S. Provisional Patent Application No. 62/307,779, entitled "System and Method for Guiding and Tracking a Region of Interest Using an Endoscope" and filed on Mar. 14, 2016, for priority.

The aforementioned application is incorporated herein by reference in its entirety.

FIELD

The present specification relates generally to endoscopes, and more specifically, to a system and method for repositioning a region of interest from a first location to a second location on at least one display screen of the endoscope.

BACKGROUND

An endoscope is a medical instrument used for examining and treating internal body parts such as the alimentary canals, airways, the gastrointestinal system, and other organ systems. Conventionally used endoscopes comprise an insertion tube, either flexible or rigid, carrying illuminators such as light-emitting diodes (LED) or a fiber optic light guide for directing light from an external light source situated at a proximal end of the tube to a distal tip. Also, most endoscopes are equipped with one or more channels through which medical devices, such as forceps, probes, and other tools, may be passed. Further, during an endoscopic procedure, fluids, such as water, saline, drugs, contrast material, dyes, or emulsifiers are often introduced or evacuated via the insertion tube. A plurality of channels, one each for introduction and suctioning of liquids, may be provided within the insertion tube.

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, bronchoscope, laparoscopy, upper gastrointestinal (GI) endoscopy among others. Endoscopes may be inserted into the body's natural orifices or through an incision in the skin.

Endoscopes, that are currently being used, typically have a front camera for viewing the internal organ, such as the colon, and an illuminator for illuminating the field of view of the camera. Some endoscopes also comprise one or more side cameras and the corresponding illuminators for viewing the internal organs that are not in direct field of view of the front camera. The camera(s) and illuminators are located in a tip of the endoscope and are used to capture images of the internal walls of the body cavity being endoscopically scanned. The captured images are sent to a control unit coupled with the endoscope via one of the channels present in the insertion tube, for being displayed on a screen coupled with the control unit.

While endoscopes help in the detection and cure of a number of diseases in a non-invasive manner, conventional endoscopes suffer from the drawback of having a limited field of view. The field of view is limited by the narrow internal geometry of organs as well as the insertion port, which may be body's natural orifices or an incision in the skin. The image of the body cavity captured by the cameras such as a front camera is displayed on a display screen coupled with the camera. Sometimes irregularities such as polyps are observed forming on internal walls of a body cavity being scanned. A clear display of the polyp during an endoscopic procedure such as colonoscopy is important in order to enable a medical practitioner to operate on the polyp by inserting medical tools via the working channel of the endoscope. It is advantageous to position a region of interest like the polyp in a distinct location such as a center of the display screen while operating on the polyp.

It is often difficult to maintain the display of the polyp constantly in the center of the display screen due to the movement of the body cavity, such as the colon, in which the polyp may be detected. It may also be beneficial for the medical practitioner to record the location of the polyp for operating upon it in the future.

For accurately and easily operating upon a region of interest within a body cavity endoscopically, it is essential that the location of the display of the region of interest within an image captured by the endoscope be maintained constantly at a desired location all through the endoscopic procedure.

Hence, there is need for a method enabling an operating medical practitioner to maintain the position of the region of interest at a desired location, such as in the center of the display screen, during an endoscopic procedure.

SUMMARY

In some embodiments, the present specification discloses a method of displaying a region of interest within an endoscopic image on a target area of a pre-defined display screen of an endoscopy system comprising an insertion portion having a tip section with at least one viewing element for capturing images of a body cavity comprising the region of interest, the display screen being coupled with the at least one viewing element, the method comprising: detecting the region of interest on a wall of the body cavity; displaying the region of interest on the display screen; marking the region of interest on the display screen; determining a transformation to be applied to the region of interest; and applying the determined transformation for causing the region of interest to be displayed on a target area of the pre-defined display screen.

Optionally, the target area comprises the center of the display screen.

Optionally, the region of interest is a body abnormality.

Optionally, the region of interest is a polyp.

Optionally, the pre-defined display screen is a central display screen coupled with a front viewing element of the endoscopy system and wherein the endoscopy system comprises a working channel located proximate to the front viewing element.

Optionally, marking the region of interest comprises selecting the region of interest by using a graphical user interface (GUI). Still optionally, marking the region of interest comprises selecting the region of interest by using a mouse click, a touch screen, a hand gesture, or eye tracking.

Optionally, determining a transformation to be applied to the region of interest comprises determining an angle between the region of interest and the viewing element.

Optionally, applying the determined transformation comprises providing guidance to manually move the tip section of the insertion portion of the endoscope for positioning the region of interest in a target area of the display screen.

Optionally, applying the determined transformation comprises automatically moving the tip section of the insertion portion of the endoscope for positioning the region of interest in a target area of the display screen.

In some embodiments, the present specification discloses an endoscope comprising an insertion portion having a tip section with at least one viewing element for capturing images of a body cavity comprising a region of interest, the at least one viewing element being coupled with a display screen, the display screen being coupled with a processor for performing a sequence of steps for displaying the region of interest within an endoscopic image on a target area of the display screen, the sequence of steps comprising: detecting the region of interest on a wall of the body cavity; displaying the region of interest on a display screen; marking the region of interest on the display screen; determining a transformation to be applied to the region of interest; and applying the determined transformation for causing the region of interest to be displayed in the center of the pre-defined display screen.

In some embodiments, the present specification discloses a method of repositioning a region of interest from a first location to a second location on a display screen of an endoscopy system comprising: selecting a first location comprising a detected region of interest on the display screen; selecting a second location on the display screen; estimating a transformation to be applied to cause said region of interest to move in the direction of said second location; applying said estimated transformation; and evaluating if the region of interest is displayed at said second location on the display screen and if said region of interest is not displayed at said second location, repeatedly estimating a new transformation based on the most recent location of the region of interest and applying the same to cause said region of interest to be displayed at said second location on the display screen.

In some embodiments, said first location and said second location may be on the same display screen. Optionally, said first location is on a first display screen and said second location is on a second display screen. Optionally, said second location is substantially the center of the display screen or it is the focal point of the images being captured by the viewing elements of an endoscope during an endoscopic procedure.

Optionally, said region of interest is a body abnormality. Optionally, said region of interest is a polyp.

Optionally, said first and second locations are selected by using a graphical user interface (GUI). Optionally, said first and second locations are selected by using a mouse click, a touch screen, a hand gesture, or eye tracking.

Optionally, said estimation of transformation to be applied to the region of interest comprises determining an angle between the region of interest and the viewing element.

Optionally, applying the estimated transformation comprises providing guidance to manually move the tip section of the insertion portion of the endoscope for positioning the region of interest to said second location of the display screen.

Optionally, applying the estimated transformation comprises automatically moving the tip section of the insertion portion of the endoscope to reposition the region of interest to said second location of the display screen.

Optionally, said automatic application comprises using electrical motors to move the tip section.

In some embodiments, the present specification discloses an endoscope system comprising: an insertion tube coupled to a distal tip section wherein said distal tip section comprises at least one viewing element; a main control unit coupled to said insertion tube and coupled to at least one display screen; a means for selecting a region of interest at a first location on said display screen; a means for selecting a second/target location on said display screen; a controller for estimating a transformation based on the most recent location of said region of interest and causing said transformation to be applied to cause said region of interest to move in the direction of said second location; and, wherein after every application of said transformation the system evaluates the latest position of said region of interest and in case said region of interest is not positioned at such second location, a new transformation is estimated based on the most recent location of the region of interest and the same is applied to cause said region of interest to move in the direction of said second location.

The aforementioned and other embodiments of the present specification shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

Figure 1:
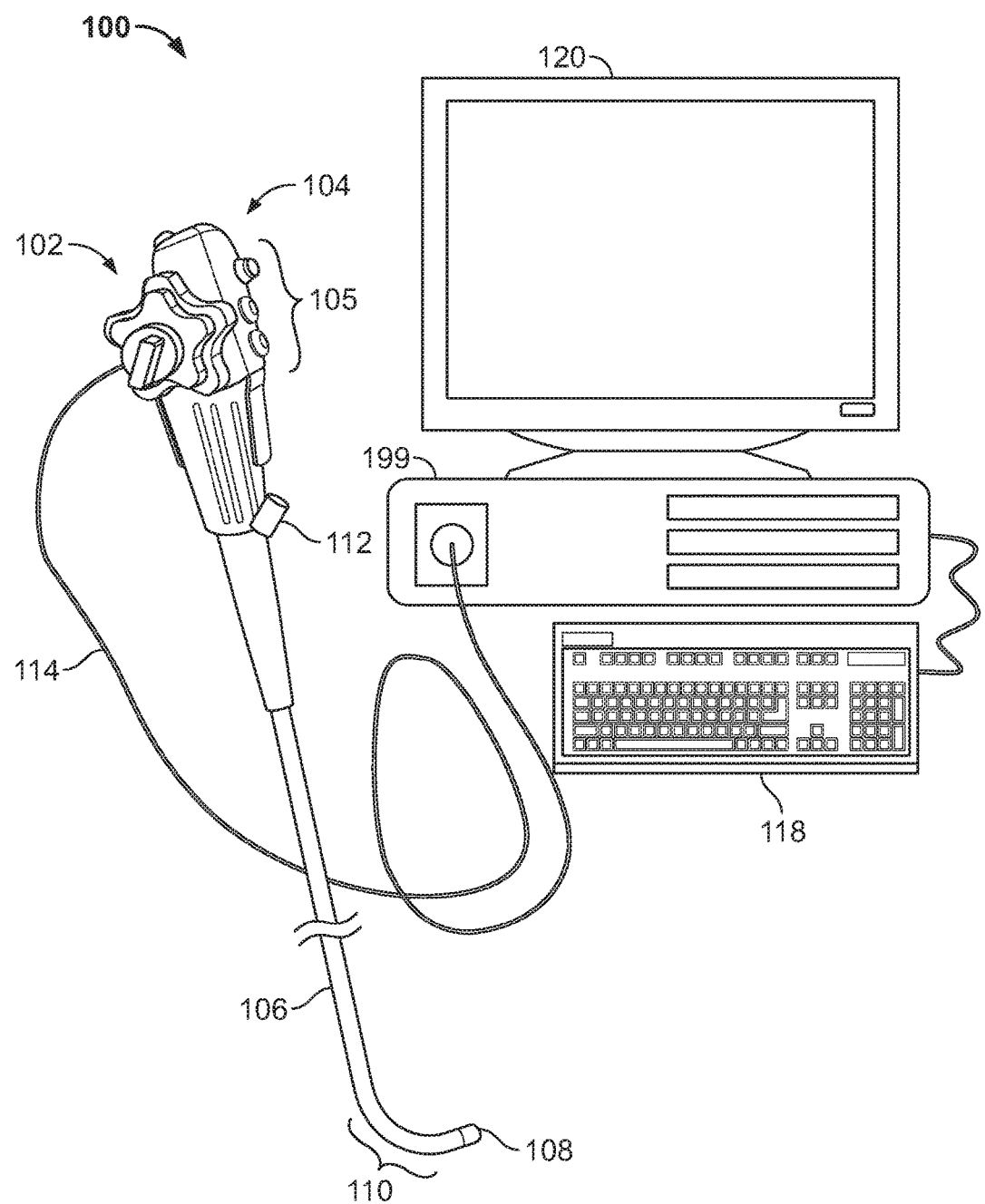
FIG. 1 illustrates a multiple viewing element endoscopy system, according to some embodiments of the present specification.

The present specification provides a system and a method for displaying a region of interest (ROI) in the image captured by a viewing element of the endoscope at a user defined location on the display screen of the endoscope. In an embodiment, the user identifies a region of interest (ROI) such as a polyp (or any other abnormality) at a first location in the image displayed on the display screen of the endoscope. The user then identifies a second, target location on the display screen at which the image should be repositioned. Consequently, the entire image is repositioned such that the region of interest (ROI) is displayed at the second location identified on the display screen. In an embodiment, the second location is substantially the center of the display screen or it is representative of the focal point of the images being captured by the viewing elements of an endoscope during an endoscopic procedure.

In an embodiment comprising an endoscopy system with multiple display screens, the first location is on a first screen and the second location is on a second screen. In an embodiment, the first screen displays the images captured by a side viewing element or camera and the second screen displays the images captured by a front viewing element or camera of the endoscopy system. In an embodiment, the first screen displays the images captured by a front viewing element or camera and the second screen displays the images captured by a side viewing element or camera of the endoscopy system. In some embodiments, a first screen may display images captured by a first side viewing element, a second screen (positioned in the center) may display images captured by a front viewing element, and a third screen may display images captured by a second side viewing element. It should be understood that any number of discrete displays may be employed to accommodate each camera or viewing element and the images captured can be displayed on any corresponding display, either dedicated or set by the user.

In an embodiment, the ROI may denote an abnormality such as a polyp detected in a body cavity which the user may want to continuously track or display prominently during a medical procedure. The present specification allows a user to view an image of the detected polyp on the center of a display or screen or on a central and/or front screen of the endoscopy system where the system has more than one display, thereby making operating upon the polyp much easier. In embodiments, the present specification allows a user to view an image of a detected polyp at a target region in the display screen.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise. It should be noted herein that any feature or component described in association with a specific embodiment may be used and implemented with any other embodiment unless clearly indicated otherwise.

FIG. 1 illustrates a multi-viewing element endoscopy system in which the method and system for repositioning a region of interest (ROI) from a first location to a second location such as the center of a display or as the focal point of images being captured by the viewing elements of an endoscope during an endoscopic procedure may be implemented. As would be apparent to persons of skill in the art, the method and system for repositioning a region of interest (ROI) from a first location to a second location such as the center of images being captured by the viewing elements of an endoscope during an endoscopic procedure may be implemented in any endoscope comprising one or more viewing elements for capturing images of the insides of a body cavity. Further, the method and system for keeping a region of interest (ROI) in the center of images being captured by the viewing elements of an endoscope during an endoscopic procedure may be implemented in any endoscope system comprising at least one display screen.

Reference is now made to FIG. 1, which shows a multi-viewing elements endoscopy system 100. System 100 may include a multi-viewing elements endoscope 102. Multi-viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted. In embodiments, the handle 104 also includes one and more side service/working channel openings.

Tip 108 may include multi-viewing elements. In accordance with an embodiment, tip 108 includes a front viewing element and one or more side viewing elements. In another embodiment, tip 108 may include only a front viewing element.

In addition, tip 108 may include one or more service/working channel exit point. In accordance with an embodiment, tip 108 includes a front service/working channel exit point and at least one side service channel exit point. In another embodiment, tip 108 may include two front service/working channel exit points.

A utility cable 114, also referred to as an umbilical tube, may connect between handle 104 and a Main Control Unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199.

In the embodiment shown in FIG. 1, the main control unit 199 comprises a screen/display 120 for displaying operation information concerning an endoscopy procedure when the endoscope 102 is in use. The screen 120 may be configured to display images and/or video streams received from the viewing elements of the multi-viewing element endoscope 102. The screen 120 may further be operative to display a user interface for allowing a human operator to set various features of the endoscopy system.

Optionally, the video streams received from the different viewing elements of the multi-viewing element endoscope 102 may be displayed separately on at least one monitor (not seen) by uploading information from the main control unit 199, either side-by-side or interchangeably (namely, the operator may switch between views from the different viewing elements manually). Alternatively, these video streams may be processed by the main control unit 199 to combine them into a single, panoramic video frame, based on an overlap between fields of view of the viewing elements. In an embodiment, two or more displays may be connected to the main control unit 199, each for displaying a video stream from a different viewing element of the multi-viewing element endoscope 102. The main control unit 199 is described in U.S. patent application Ser. No. 14/263,896, entitled "Method and System for Video Processing in a Multi-Viewing Element Endoscope" and filed on Apr. 28, 2014, which is herein incorporated by reference in its entirety.

Figure 2:
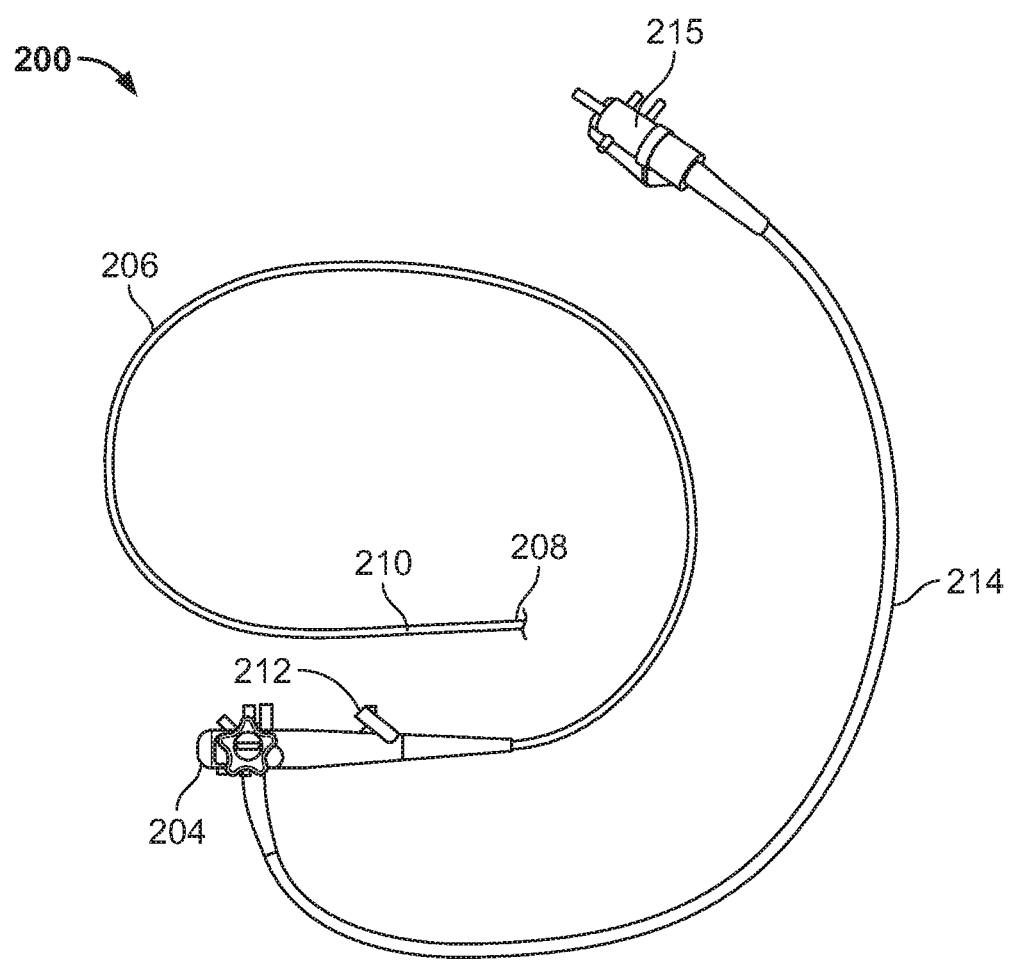
FIG. 2 is an illustration of an endoscope in which the method and system of the present specification may be implements, in accordance with an embodiment.

FIG. 2 illustrates another view of an endoscope in which the method and system for repositioning a region of interest from a first location to a second location on the display screen of the endoscope may be implemented. Endoscope 200 comprises a handle 204, from which an elongated shaft 206 emerges. Elongated shaft 206 terminates with a tip section 208 which is turnable by way of a bending section 210. The tip section 208 comprises at least one viewing element which is used to capture images of the body cavity which are then displayed on a display screen coupled with the viewing element. Handle 204 may be used for maneuvering elongated shaft 206 within a body cavity. In various embodiments, handle 204 comprises a service channel opening 212 through which a medical tool may be inserted. Further in various embodiments, tip 208 includes at least one service/working channel exit point from which the medical tool exits and is placed in close proximity to a region of interest/polyp on a wall of the body cavity being endoscopically examined. A utility cable 214 is used to connect handle 204 with a controller (not shown) via an electrical connector 215. The controller governs power transmission to the tip section 208. In an embodiment the controller also controls one or more fluid, liquid and/or suction pump which supply corresponding functionalities to endoscope 200. One or more input devices, such as a keyboard, a computer, a touch screen, a voice recognition system and the like, may be connected to the controller for the purpose of user interaction with the controller.

The method and system of the present specification may be applied to a multiple viewing elements endoscope having a front viewing element and side viewing elements. The method and system of the present specification enable a user to locate a polyp in a body cavity using a viewing element and then have the polyp displayed at a target location on a display screen coupled with the viewing element while operating on the polyp using medical tools inserted via a working channel of the endoscope located in proximity to the viewing element. The description provided herein is directed towards an endoscope having a working channel located near a front viewing element/camera so that a polyp observed in a body cavity, such as a colon, is displayed on a front display screen of the endoscope. However, it will be apparent to persons of skill that the method and system of the present specification can easily be applied to an endoscope having a side working channel, wherein the polyp is observed via a side viewing element positioned near the side working channel. In an embodiment, the system and method of the present specification also allows a user to identify the region of interest, such as a polyp, at a first location on a first screen and subsequently identify a second location on a second screen such that the system displays the region of interest at the second location on the second screen of the endoscope.

Figure 3A:
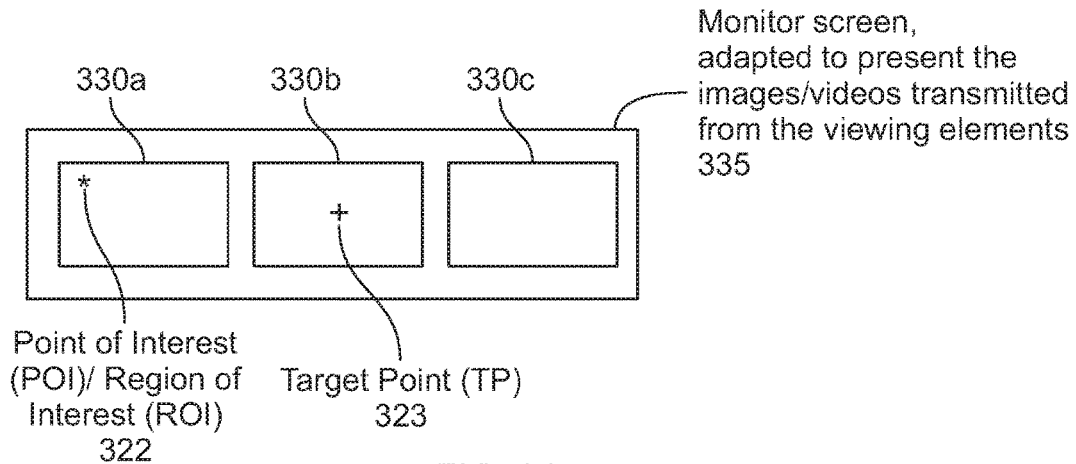
FIG. 3A is an exemplary schematic diagram showing a point of interest detected by a side viewing element and a chosen target point on a front viewing display screen of a multiple camera endoscope in accordance with an embodiment of the present specification.

FIG. 3A is an exemplary schematic diagram showing a point of interest detected by a side viewing element and a chosen target point on a front viewing display screen as can be seen using a multi-viewing element endoscope, such as the multi viewing element endoscope 102 described in FIG. 1. Referring to FIG. 1 and FIG. 3a, multi-viewing element endoscope 102, is connected to the controller 199 through a utility cable 114. In embodiments, endoscope 102, provides three simultaneous endoscopic views using three cameras housed in the tip 108, of endoscope 102. Controller 199 is connected to three display screens, 330a, 330b, and 330c, wherein each display screen may be configured to display a corresponding view of the three endoscopic views provided by endoscope system 102. In an embodiment, the display screen 330b displays the view captured by a front camera and the display screens 330a and 330c display the views captured by two side cameras housed in tip 108 of the endoscope 102. In some embodiments, display screens 330a, 330b, and 330c are in the form of a single large screen 335. In some embodiments, the videos are either separated one for the other or stitched together to form a panoramic view.

In an embodiment, during an endoscopic procedure there is an interest to keep a certain point of interest/region of interest (ROI) 322, shown on side display 330a, in the center display screen 330b and more specifically at a target point (TP) 323 located on the center display screen 330*b*. For example, during an abnormality/polyp treatment, the abnormality should be located in front of the center viewing element, such that a medical tool emerging from the front working channel is easily detected by the front viewing element. In another embodiment, wherein the scope has a side working channel the abnormality should preferably be located in front of the side viewing element, such that a medical tool emerging from the side working channel is easily detected by the side viewing element. However, due to the movement of either the colon or multiple viewing elements, this task is not trivial and consumes time during the procedure. In subsequent sections, the present specification discloses systems and methods to enable displaying the ROI 322 at the required TP 323 on a specific display screen.

Figure 3B:
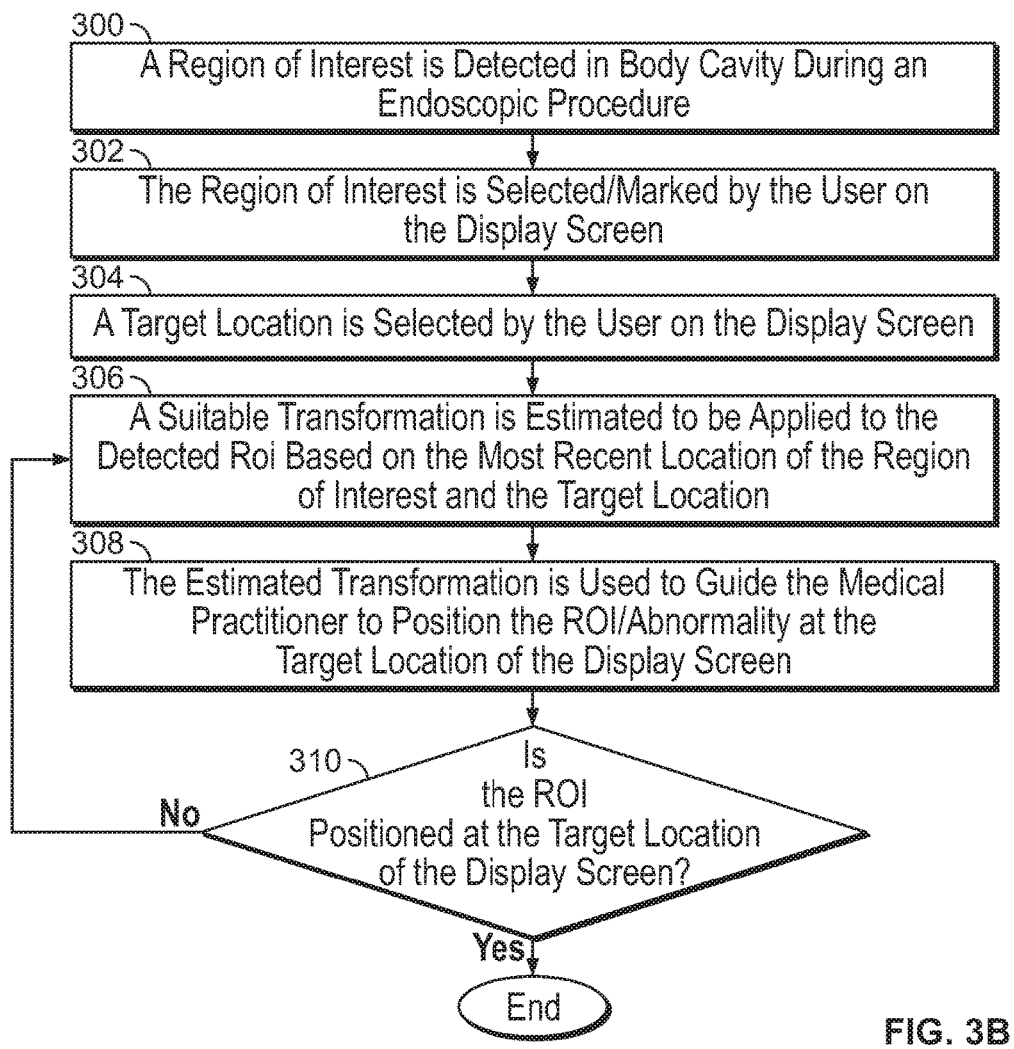
FIG. 3B is a flowchart describing a method of repositioning a region of interest (ROI) from a first location on a display screen of the endoscope to a second location on at least one display screen, in accordance with an embodiment of the present specification.

FIG. 3B is a flowchart depicting a method of repositioning a region of interest (ROI) from a first location on a display screen of the endoscope to a second location on the same display screen or on another display screen of the endoscope, in accordance with an embodiment of the present specification. At step 300 a region of interest (ROI) is detected in the body cavity during an endoscopic procedure. In various embodiments a ROI is an abnormality, such as a polyp, a lesion, that may be detected in a body cavity such as a colon. The abnormality is detected via a viewing element of the endoscope such as a front camera and or a side camera and displayed on the display screen of the endoscope. In an embodiment wherein the endoscope comprises a working channel located in proximity of a front viewing element/camera, there is an interest to keep the detected abnormality within the field of view of the front viewing element, which is in data communication with the front display screen.

At step 302, the region of interest is identified by selecting/marking the same on the display screen. In an embodiment, the ROI is identified and marked by using a graphical user interface (GUI). In various embodiments, the medical practitioner may mark the ROI/polyp using known methods such as by a mouse click, a touch screen, a hand gesture, or eye tracking. Specifically, upon visually noticing a point of interest 322 on a display screen, a user may navigate an icon on the display to visually coincide with the displayed point of interest 322, resulting in an icon being visually superimposed over the point of interest 322. When a user clicks on the icon, now visually superimposed over the point of interest 322, the display coordinates of the icon are recorded by a processor in memory and those coordinates are associated with the displayed position of the point of interest 322.

In an embodiment, the endoscopy system comprises an integrated mouse on the scope handle which is used by the user to select an ROI. In an embodiment, the ROI is detected and marked using image tracking algorithms known in the art, such as the Lucas-Kanade algorithm. In another embodiment, the ROI is detected and marked by matching various neighboring pixels contained in that specific area of the image in accordance with their normalized cross correlation with surrounding areas. In another embodiment, the ROI may be detected by using one or more sensors incorporated in the insertion tube of the endoscope. In embodiments, the system comprises sensors such as an accelerometer or a gyroscope or an electromagnetic tracker or a combination of these sensors. In various embodiments, at least one sensor is used together with the camera to assess the location of a target or ROI relative to the camera. For example, in an embodiment, using an accelerometer, a three-dimensional scene is constructed using displacement estimation from two images taken at different locations and/or from different cameras. In some embodiments, structured light-based 3D estimation is used for 3D scene construction and assessment. In addition, the location of the sensor is important in various embodiments. For example, in an embodiment, an accelerometer must be placed with in the distal tip such that it has the same motion as the camera. In another embodiment, a structured light emitter must have the largest parallax possible from the camera.

At step 304, a second/target location at which the region of interest is to be positioned is selected on the display screen. In an embodiment, the second location is positioned on the same display screen. In another embodiment comprising an endoscope with multiple display screens, the second location is positioned on a second display screen. In an embodiment, the target location is identified and marked by using a graphical user interface (GUI). In various embodiments, the medical practitioner may mark the target location using known methods such as by a mouse click, a touch screen, a hand gesture, or eye tracking. Specifically, upon visually identifying a target point 323 on a display screen, a user may navigate an icon on the display to visually coincide with the target point 323, resulting in an icon being visually superimposed over the target point 323. When a user clicks on the icon, now visually superimposed over the target point 323, the display coordinates of the icon are recorded by a processor in memory and those coordinates are associated with the target point 323. In an embodiment, the endoscopy system comprises an integrated mouse on the scope handle which is used by the user to select the target location. In some embodiments, the target point is positioned in the center of the display screen. In other embodiments, the target point is not positioned in the center of the display screen.

At step 306 a suitable transformation to be applied to the detected ROI is estimated. In an embodiment, applying the transformation to the detected ROI comprises determining an angle between the ROI and the viewing element/camera. The angle may be determined by using a camera calibration method. The calibration method comprises mapping each pixel in an image captured by the camera with a vector connecting a center of the camera lens with the outside world.

At step 308 the transformation estimated in step 306 is used to guide the user to position the ROI/abnormality at the target point (TP) or the second location of the display screen and maintain the position while operating upon the abnormality by inserting medical tools via the working channel. In various embodiments, the transformation or movement to the second location is estimated in a distance of millimeters from the first location or at an angle relative to the first location. Exemplary transformations include pulling the distal tip 5 mm backward or moving the distal tip 30° to the left. In some embodiments, any transformation that places the ROI in the target location is acceptable. In an embodiment, the user is guided by means of icons, guides, or other data displayed on a graphical user interface (GUI) which directs a user to manually move the distal tip of the insertion portion of the endoscope in order to position the abnormality in the target region of the display screen. In another embodiment, the distal tip is moved automatically based on the applied transformation to position the abnormality in the target region of the display screen. In an embodiment, in an automatic system, electronic motors are used to move the distal tip and facilitate the transformation. In yet another embodiment, the abnormality is positioned in the target region of the display screen by using a combination of manual and automatic methods. In an embodiment comprising a semi-automatic system, the angular rotation of tip section is automatic while the longitudinal movement of complete insertion tube in manually done by the user. At step 310 it is determined if the ROI is positioned at the target point of the display screen. If the ROI is not located in the target point the method steps 306 to 310 are repeated.

Figure 3C:
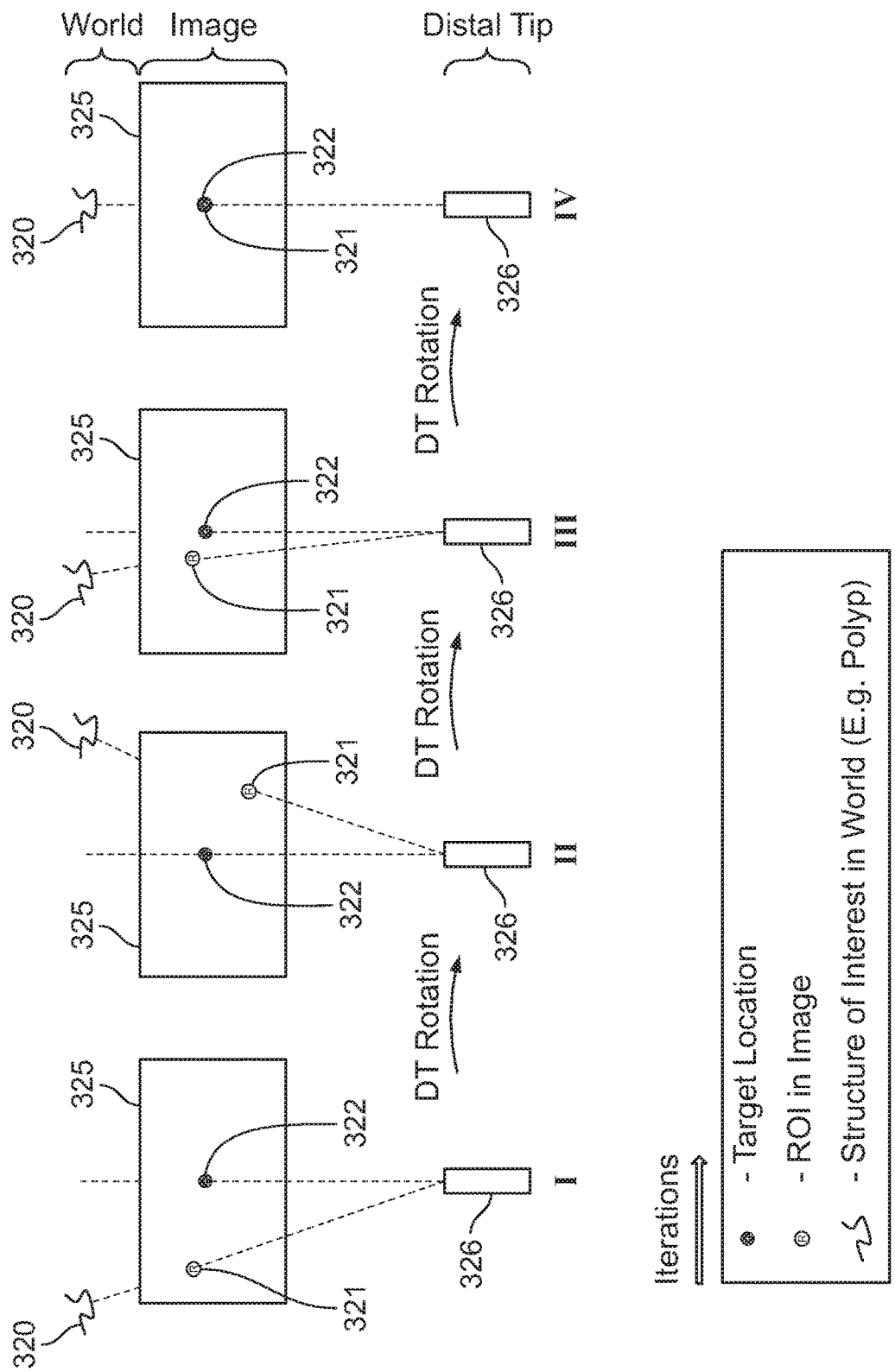
FIG. 3C illustrates a navigation process to move a region of interest detected by a side pointing camera and displayed at a first location on display screen to a target point located at a second location on a display screen in accordance with an embodiment of the present specification.
Figure 3D:
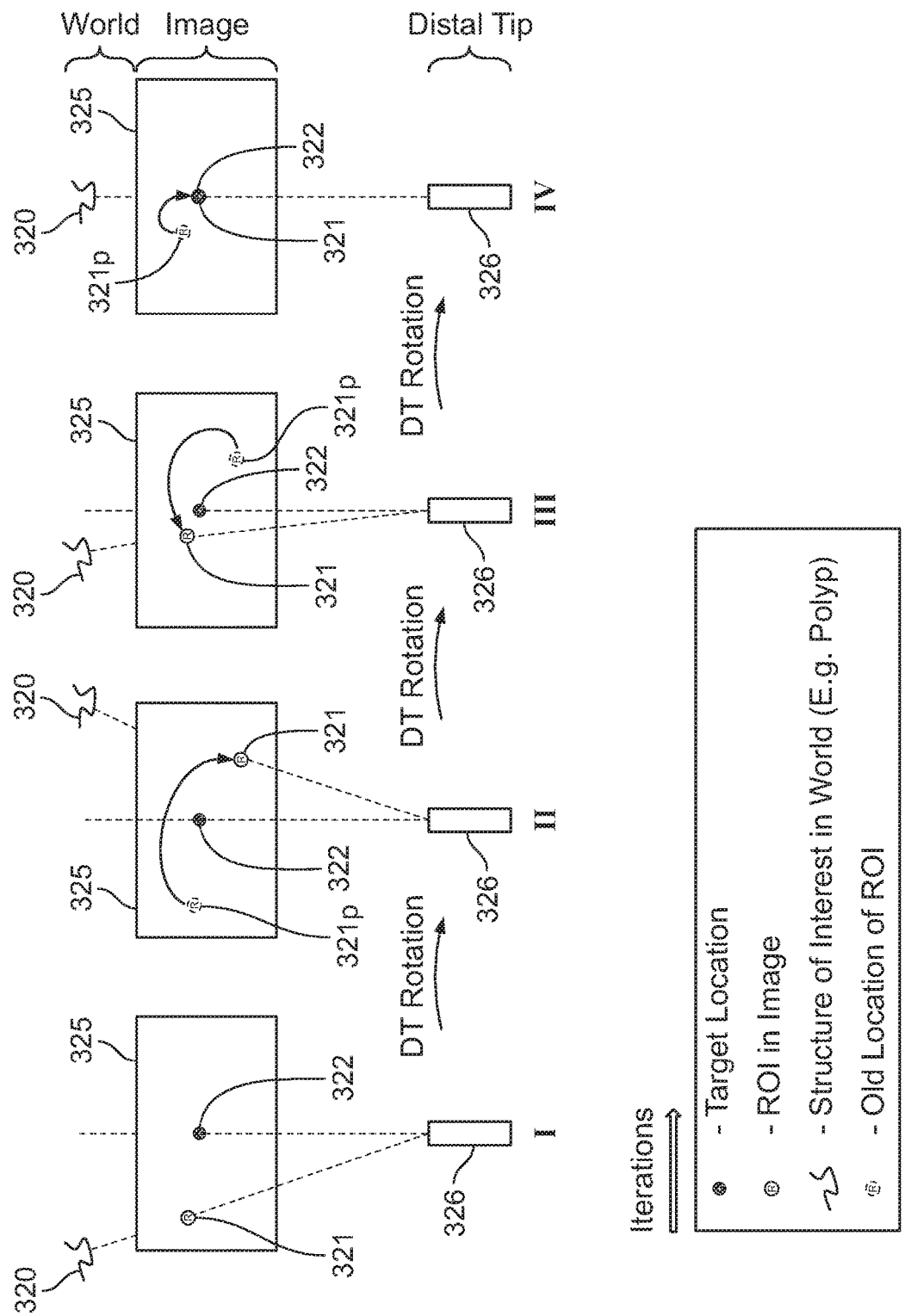
FIG. 3D illustrates the navigation process as depicted in FIG. 3C wherein the incremental movement of ROI towards the target point is shown in each image snapshot in accordance with an embodiment.

FIG. 3C and FIG. 3D illustrate a navigation process to move a region of interest from a first location on the display screen to a target point/second location on the display screen, in accordance with an embodiment of the present specification. In FIG. 3C, a structure of interest (polyp) 320 is shown at the top of the image 325. The polyp 320 is captured in the image at a point 321 which is termed as the region of interest (ROI). The goal of the navigation method of the present specification is to move the distal tip 326 of an endoscope capturing the image 325, such that the image ROI 321 is shifted to a desired target region 322, which in an embodiment is in the center of the image. As shown in the figure, the distal tip 326 is required to be rotated in a clockwise direction. This is done in via a feed-back process, wherein at each step the position of the ROI is detected and a transformation is computed and is used to move the distal tip 326 to bring ROI 321 as near as possible to the target region 322. In FIG. 3C, four different image snapshots I, II, III and IV are shown that represent the position of ROI at four different time steps such that at each step a unique transformation is computed based on the position of the ROI at that time. Image snapshot I represents the starting position of the ROI and the target position, and in each subsequent snapshot, due to the movement of the distal tip 326 controlled by computed transformations, the ROI 321 is positioned closer to the target position as compared to the previous snapshot. Finally, in snapshot IV, the ROI 321 is positioned in the target region 322. One of ordinary skill in the art can appreciate that the number of steps required to bring the ROI over the target region can vary depending on the starting positions of the ROI and the target region and the efficiency and accuracy of the system deployed for facilitating the navigation process. In an embodiment, the system has an option wherein a user can lock the position of ROI once it is positioned at the desired point in the display screen. In an embodiment, the position of the ROI is locked by monitoring the movements of the endoscope and applying a compensation, based on said movements, to the distal tip. Once the position of ROI is locked, subsequently, the ROI is always shown at the same location on the display screen irrespective of the movement of the tip section of the endoscopy system.

In embodiments, the transformation can be applied automatically or manually. In case an automatic transformation is applied, electrical motors rotate the distal tip in the desired directions, and/or push/pull the insertion tube in and out. In case a manual transformation is applied, the user gets the transformation instructions by an API (Application Program Interface) and applies them directly to the distal tip. An example for such API can be implemented by showing the user a scheme of the scope knobs with arrows that indicate the transformation direction. In an embodiment, the direction and length of the arrows change dynamically as they indicate the desired transformation needed to be performed in each step.

FIG. 3D also illustrates the navigation process as depicted in FIG. 3C wherein the incremental movement of ROI towards the target region is clearly shown in each image snapshot. In the image snapshots II, III and IV, shown in FIG. 3D, the current position of ROI is shown as 321 while the last position of ROI (prior to application of last transformation) is depicted as 321p.

Figure 4:
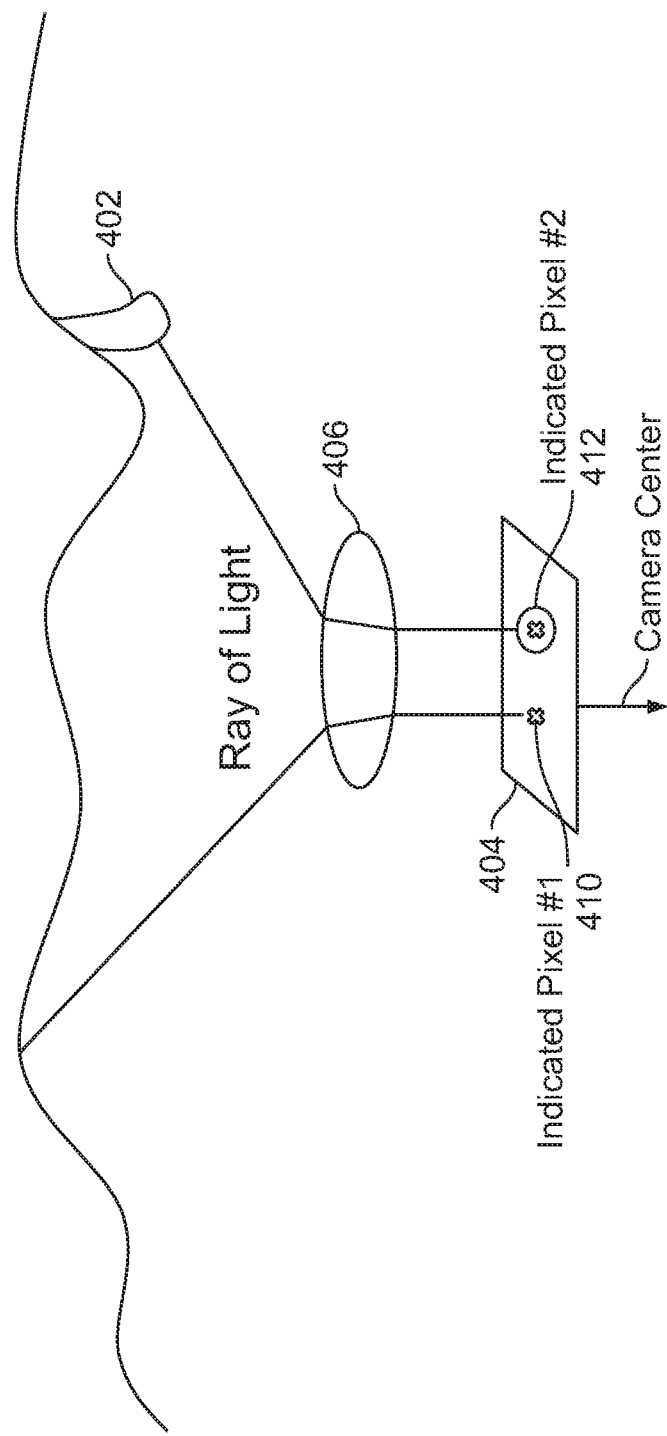
FIG. 4 illustrates a camera calibration method, in accordance with an embodiment of the present specification.

FIG. 4 illustrates a camera calibration method for determining the transformation to be applied to an endoscope tip for moving a region of interest to a target point on the display, in accordance with an embodiment of the present specification. A camera (in the endoscope's tip) is calibrated for obtaining a transformation to be applied to move the endoscope tip, and thereby the region of interest to the target point. The calibration method comprises mapping each pixel in an image captured by the camera with a vector connecting a center of the camera lens with the outside world. During the calibration process a ray orientation pixel mapping is obtained with respect to an object/abnormality 402 in the outside world by measuring a distance between the object/abnormality 402 and a pixel 410 located in its image 404 taken by a camera lens 406. Similarly, a ray orientation pixel mapping is obtained by measuring a distance between the object/abnormality 402 and another pixel 412 located in the image 404. By obtaining multiple such mappings with respect to a camera, the calibration parameters of the camera may be obtained by using a camera calibration algorithm. In an embodiment of the present specification, Zhang algorithm/method is used for the purpose of camera calibration. The camera calibration provides information on where a 3D object located at some coordinate relative to the camera would appear in the image. To estimate the transformation, a location of where the image would appear in the camera, given some transformation applied to the image, is estimated. The camera parameters for the estimation are obtained by calibration. An optimization process is then performed to improve the transformation until a suitable transformation is reached.

FIGS. 5A to 5G illustrate a schema demonstrating the steps for maintaining a ROI in a center of a front display screen of an endoscopy system, in accordance with an embodiment of the present specification. It should be understood by those of ordinary skill in the art that the methods of the present specification can be employed with systems having any number of screens. In an embodiment, the endoscopy system has more than one display screen. In another embodiment, the endoscopy system comprises only one screen and in this case the ROI can be positioned at a central focal point (or any other target region provided by the user) for the ease of viewing and operation.

Figure 5A:
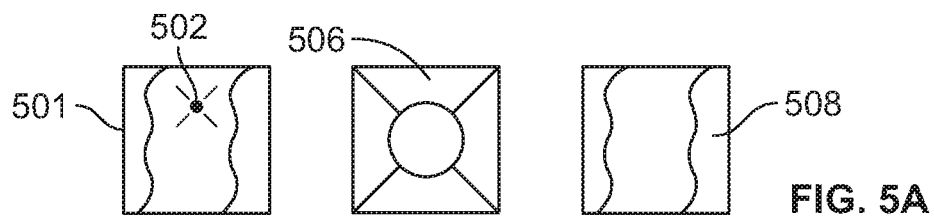
FIG. 5A illustrates a polyp located on the wall of a body cavity, such as a colon, that can be seen using a viewing element of an endoscope.

FIGS. 5A-5G illustrates displays associated with a left side camera 501, a front camera 506 and a right side camera 508 respectively. First, an insertion portion of an endoscope is inserted into a body cavity and the internal walls of the cavity are examined by a medical practitioner via the endoscopic images displayed on a monitoring screen coupled with a viewing element located in the tip of the insertion portion, until a polyp is observed on an internal wall of the body cavity. FIG. 5A illustrates a polyp 502 located on the wall of a body cavity such as a colon captured via a viewing element of an endoscope. Next the medical practitioner selects and marks the polyp as a region of interest, as discussed above.

Figure 5B:
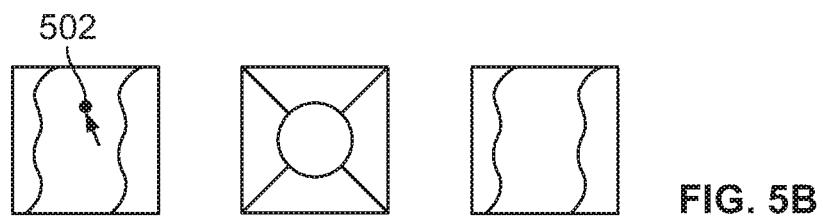
FIG. 5B illustrates the polyp of FIG. 5A marked as a ROI.

FIG. 5B illustrates the polyp 502 marked as a ROI. In an embodiment, the ROI may be selected and marked by using a graphical user interface (GUI). In various embodiments, the medical practitioner may mark the ROI/polyp 502 using known methods such as by a mouse click, a touch screen, a hand gesture, or eye tracking. In an embodiment, the endoscopy system comprises an integrated mouse on the scope handle which is used by the user to select ROI 502. In various embodiments, the marked ROI is detected by a software program running on a processor coupled with the endoscope and the monitoring screen by using any suitable image detection method.

Figure 5C:
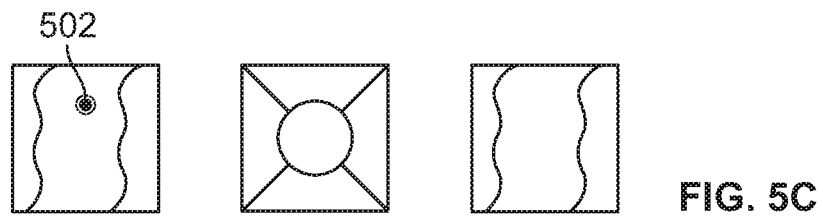
FIG. 5C illustrates the polyp/ROI of FIG. 5B detected by using an image detection algorithm.

FIG. 5C illustrates the polyp/ROI 502 being detected by using an image detection algorithm. In an embodiment, upon detection of the ROI an arrow 504 appears on the central display monitor 506 of the endoscopy system as shown in FIG. 5D.

Figure 5D:
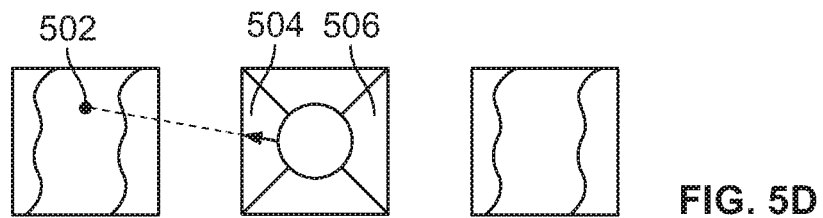
FIG. 5D illustrates a guiding arrow on a central display screen.

FIG. 5D illustrates guiding arrow 504 on central display screen 506. The arrow 504 guides the medical practitioner to move tip of the endoscope in a direction that would enable the ROI to be displayed in the center of the central display screen 506. A direction of rotation is computed by determining the rotational direction between the direction of the camera corresponding to the target point and the camera corresponding to the ROI. In an embodiment, the amount of movement in the computed direction is computed in a feedback loop, where real time sampling determines the new rotation direction, which is computed and a small rotation in this direction is applied.

In an embodiment of the present specification comprising a calibrated camera, the rotational or angular direction between the camera center, the z-axis and any pixel in the image is known. Thus, one can compute the angle between the camera, the ROI and the target location in the image and, accordingly, the rotation that should be applied to the camera to put the ROI on the target location can be estimated. After applying the transformation, the new ROI location is detected in the image and the process is repeated in an iterative manner until the ROI is placed on top of the target. An illustrative navigation process to reposition a ROI (region of interest) from a first location on a display screen to a TP (target point) at a second location in the same or another display screen is also described in FIG. 3C and FIG. 3D.

Figure 5E:
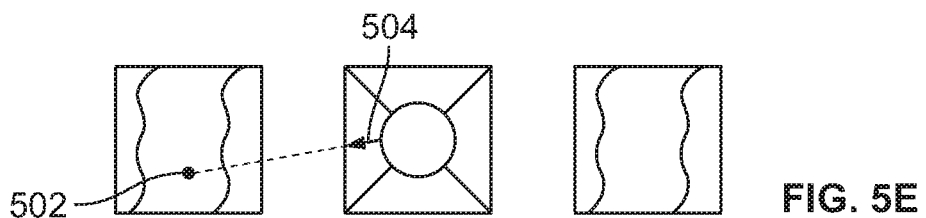
FIG. 5E illustrates the guiding arrow repositioned toward the polyp/ROI to compensate for movement of the endoscope's tip.

FIG. 5E illustrates the guiding arrow repositioned toward the polyp/ROI to compensate for movement of the endoscope's tip. Thus, FIG. 5E shows that if the endoscope's tip is moved in an upwards direction, the arrow 504 repositions pointing in a downward direction towards the polyp/ROI 502. Upon moving the endoscope tip in accordance with the direction pointed to by the arrow 504, the polyp/ROI 502 is caused to be displayed on the central display screen 506.

Figure 5F:
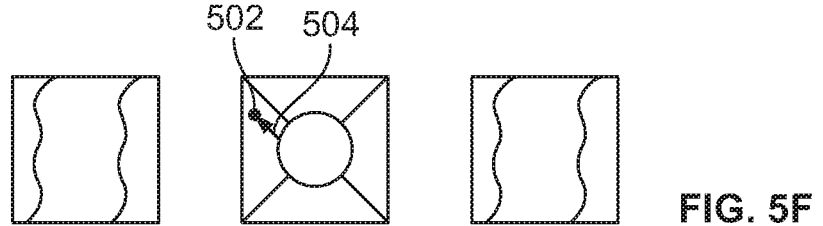
FIG. 5F is a diagram showing the polyp/ROI as it is moved so that it is displayed on a central screen with an arrow, guiding a direction of movement of the endoscopic tip in order to position the polyp/ROI in the center of the display screen.
Figure 5G:
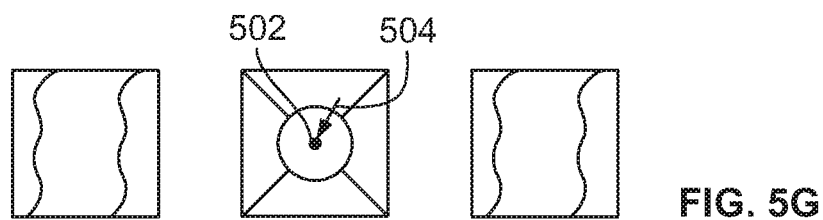
FIG. 5G illustrates the polyp/ROI positioned in the center of the central display screen.

FIG. 5F shows the polyp/ROI 502 being displayed on the central screen 506 with the arrow 504 pointing towards the direction in which the endoscope tip should be moved in order to position the polyp/ROI 502 in the center of the display screen 506. FIG. 5G illustrates the poly/ROI 502 positioned in the center of the central display screen 506. Once positioned in the center, the polyp may be operated upon easily.

Figure 6B:
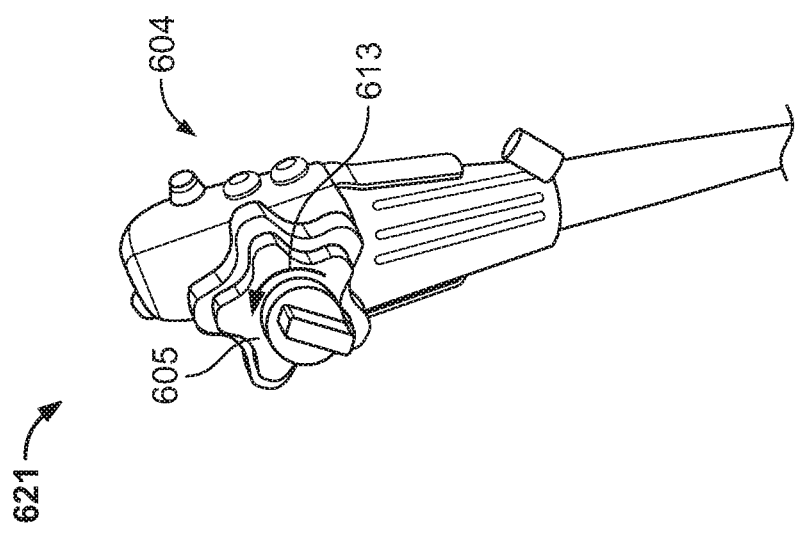
FIG. 6B illustrates an exemplary screenshot of an application program interface depicting instructions to move a knob on an endoscope handle in a counterclockwise direction, in accordance with an embodiment of the present specification.
Figure 6A:
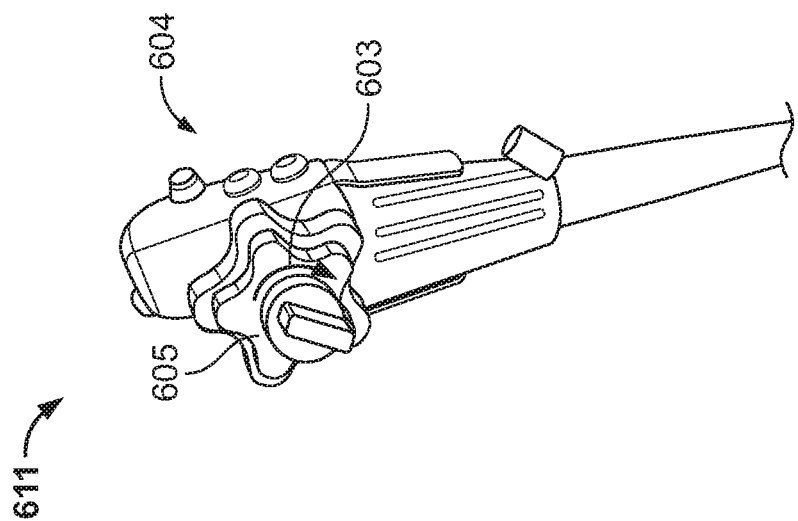
FIG. 6A illustrates an exemplary screenshot of an application program interface depicting instructions to move a knob on an endoscope handle in a clockwise direction, in accordance with an embodiment of the present specification.

FIGS. 6A and 6B illustrate exemplary screenshots 611, 621 of an application program interface depicting instructions to move a knob 605 on an endoscope handle 604 in a clockwise direction and counterclockwise direction, respectively, in accordance with an embodiment of the present specification. A display of the application program interface shows the user how to move one or more knobs of the endoscope handle in order to move the distal tip of the endoscope in the appropriate direction to position a ROI in the display screen (move the ROI to a second location). In some embodiments, referring to FIG. 6A, the application program interface uses a clockwise curving arrow 603 with text stating "Move the endoscope distally" 609 to instruct the user to rotate knob 605 in a clockwise direction to move the endoscope in a distal direction in order to position the ROI in the second location/display screen. In some embodiments, referring to FIG. 6B, the application program interface uses a counterclockwise curving arrow 613 with text stating "Move the endoscope proximally" 619 to instruct the user to rotate knob 605 in a counterclockwise direction to move the endoscope in a proximal direction in order to position the ROI in the second location/display screen. In various embodiments, the application program interface uses superimposed arrows, text, and other graphics to direct the user to move the endoscope tip in the correct direction in order to position the ROI in the second location/display screen. In various embodiments, the direction and length of the arrows or other graphics and wording of the text change dynamically as they indicate the required movements needed to position the ROI in the second location/display screen.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of displaying a region of interest within an endoscopic image on a target area of a display screen of an endoscopy system comprising an insertion portion having a tip section with at least a front viewing element and a side viewing element for capturing images of a body cavity comprising the region of interest, the display screen being coupled with the front viewing element and the side viewing element, the method comprising:

capturing an image of the region of interest through one of the front viewing element or side viewing element;

displaying the region of interest on the display screen;

recording a demarcation of the region of interest on the display screen;

recording a demarcation of the target area on the display screen;

determining a transformation to be applied to the region of interest; and applying the determined transformation to provide guidance to direct a movement of the insertion portion toward the target area based on said recorded demarcation of the target area such that the region of interest is positioned in the target area on the display.

2. The method of claim 1 wherein the target area comprises the center of the display screen.

3. The method of claim 1 wherein the region of interest is a polyp.

4. The method of claim 1 wherein the pre-defined display screen is a central display screen coupled with the front viewing element and wherein the insertion portion comprises a working channel located proximate to the front viewing element.

5. The method of claim 1 wherein a user marks the region of interest by using a graphical user interface (GUI) and selecting a portion of the pre-defined display using a mouse click, a touch screen, a hand gesture, or eye tracking.

6. The method of claim 1 wherein determining a transformation to be applied to the region of interest comprises determining an angle between the region of interest and the front viewing element.

7. The method of claim 1 wherein applying the determined transformation comprises generating and electronically displaying a visual guide that directs a movement of the insertion portion such that the region of interest moves into the target area on the display screen.

8. The method of claim 1 wherein applying the determined transformation comprises using motors in said endoscope to automatically move the insertion portion in order to position the region of interest in the target area.

9. An endoscope comprising an insertion portion having a tip section with at least one viewing element for capturing images of a body cavity comprising a region of interest, the at least one viewing element being in data communication with a display screen, the display screen being coupled with a processor for executing a plurality of programmatic instructions, stored in non-transient memory, for displaying the region of interest within an endoscopic image on a target area of the display screen, the plurality of programmatic instructions comprising:
   capturing an image of the region of interest through the at least one viewing element;
   displaying the region of interest on the display screen;
   recording a demarcation of the region of interest on the display screen;
   recording a demarcation of the target area on the display screen;
   determining a transformation to be applied to the region of interest; and
   applying the determined transformation to provide guidance to direct a movement of the insertion portion toward the target area based on said recorded demarcation of the target area such that the region of interest is positioned in the target area on the display screen.

10. The method of claim 9 wherein determining a transformation to be applied to the region of interest comprises determining an angle between the region of interest and the at least one viewing element.

11. The method of claim 9 wherein applying the determined transformation comprises generating and electronically displaying a visual guide that directs a movement of the insertion portion such that the region of interest moves into the target area on the display screen.

12. A method of repositioning a region of interest from a first location to a second location on at least one display screen of an endoscopy system, said endoscopy system having an insertion portion with at least one viewing element, comprising:
   selecting a first location comprising a detected region of interest on the at least one display screen;
   selecting a second location on the at least one display screen;
   estimating a transformation to be applied to guide a movement of said region of interest toward said second location;
   applying said estimated transformation;
   evaluating if the region of interest is displayed at said second location on the at least one display screen; and
   if said region of interest is not displayed at said second location, repeatedly estimating a new transformation based on a most recent location of the region of interest and guiding a movement of said region of interest toward said second location;
   wherein applying the estimated transformation comprises generating and electronically displaying a visual guide that directs a movement of the insertion portion such that the region of interest moves into the second location on the display.

13. The method of claim 12, wherein said first location and said second location are on one display screen.

14. The method of claim 12, wherein said second location is substantially at a center of the at least one display screen.

15. The method of claim 12, wherein said second location is at a focal point of images being captured by the at least one viewing element.

16. The method of claim 12, wherein said selecting of the first location or the selecting of the second location are achieved by detecting a mouse click, a touch screen, a hand gesture, or eye movement applied to said at least one display screen.

17. The method of claim 12, wherein said estimation of transformation to be applied to the region of interest comprises determining an angle between the region of interest and the at least one viewing element.

18. The method of claim 12, wherein applying the estimated transformation comprises using motors in said endoscope to automatically move the insertion portion in order to position the region of interest in the second location.

19. A method of repositioning a region of interest from a first location to a second location on at least one display screen of an endoscopy system, said endoscopy system having an insertion portion with at least one viewing element, comprising:
   selecting a first location comprising a detected region of interest on the at least one display screen;
   selecting a second location on the at least one display screen;
   estimating a transformation to be applied to guide a movement of said region of interest toward said second location;
   applying said estimated transformation;
   evaluating if the region of interest is displayed at said second location on the at least one display screen; and
   if said region of interest is not displayed at said second location, repeatedly estimating a new transformation based on a most recent location of the region of interest and guiding a movement of said region of interest toward said second location;
   wherein applying the estimated transformation comprises using motors in said endoscope to automatically move the insertion portion in order to position the region of interest in the second location.

* * * * *